United States Patent [19]

Barrett

[11] 3,932,663

[45] Jan. 13, 1976

[54] CERTAIN 3-AMINO-PROP-1-ENES FOR TREATING TRYPANOSOMA CRUZI INFECTIONS

[75] Inventor: Paul Anthony Barrett, Beckenham, England

[73] Assignee: Burroughs Wellcome Co., Research Triangle Park, N.C.

[22] Filed: Dec. 13, 1972

[21] Appl. No.: 314,845

[30] Foreign Application Priority Data
Dec. 29, 1971 United Kingdom............... 60315/71
Oct. 23, 1972 United Kingdom............... 48748/72

[52] U.S. Cl.............................. 424/330; 260/570 R
[51] Int. Cl.².......................................... A61K 31/135
[58] Field of Search.................. 424/330; 260/570 R

[56] References Cited
UNITED STATES PATENTS
3,345,411   10/1967   Heinrich et al..................... 424/330

*Primary Examiner*—V. D. Turner
*Attorney, Agent, or Firm*—Donald Brown

[57] ABSTRACT

3-Amino-prop-1-enes substituted in the 1-position by various specified combinations of phenyl, biphenylyl and fluorenyl groups and optionally substituted in the amino group by alkyl or benzyl groups, which have been found to be active against infections of Trypanosoma cruzi. Methods of making such compounds and pharmaceutical formulations containing the same.

36 Claims, No Drawings

CERTAIN 3-AMINO-PROP-1-ENES FOR TREATING TRYPANOSOMA CRUZI INFECTIONS

This invention relates to novel substituted 3-amino-prop-1-enes, to novel intermediates useful in their preparation and to methods of preparing the 3-amino-prop-1-enes.

The novel substituted 3-amino-prop-1-enes of the invention have been found to have a trypanocidal effect. In particular, they have been found to kill *Trypanosoma cruzi* when administered to mice infected with this organism.

Infections by *Trypanosoma cruzi*, are fairly common in South America causing Chagas' disease in humans, which disease has heretofore proved to be extremely difficult to treat effectively.

Accordingly, the present invention provides a substituted 3-amino-prop-1-ene of formula (I):

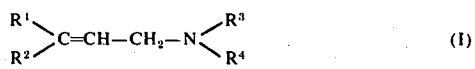
(I)

where $R^1$ and $R^2$ are the same or different and can each represent a substituted or unsubstituted biphenylyl or fluorenyl group, or one only of $R^1$ and $R^2$ can represent a substituted or unsubstituted phenyl group, with the proviso that both of $R^1$ and $R^2$ cannot represent a substituted biphenylyl group and that when one of $R^1$ and $R^2$ represents a substituted biphenylyl group the other represents a substituted or unsubstituted phenyl group; and where $R^3$ and $R^4$ are the same or different and can each represent a hydrogen atom, an alkyl group having from 1 to 4 carbon atoms or a benzyl group; or a salt thereof, especially a pharmaceutically acceptable salt thereof.

As mentioned above one or both of the $R^3$ and $R^4$ substituents may represent benzyl groups.

Examples of suitable substituents are the halo atoms and the nitrile and nitro groups.

Compounds in which $R^1$ represents a substituted 4-biphenylyl group and $R^2$ represents a substituted phenyl group have been found to be highly active. Such compounds exhibit geometrical isomerism and it should be noted that the cis isomer, i.e. the isomer of formula (II)

(II)

where $R^1$, $R^2$, $R_3$ and $R^4$ are as defined above, generally shows a higher activity, in some cases a much higher activity, than the corresponding trans isomer of formula (III)

(III)

which, in some cases, may have only a low activity against *Trypanosoma cruzi* infections. This property also applies to other compounds of the invention where the possibility of cis (the larger $R^1/R^2$ group being on the same side of the double bond as the $CH_2NR^3R^4$ group) and trans (the larger $R^1/R^2$ group being on the opposite side) exists. For example, compounds of formula (IV)

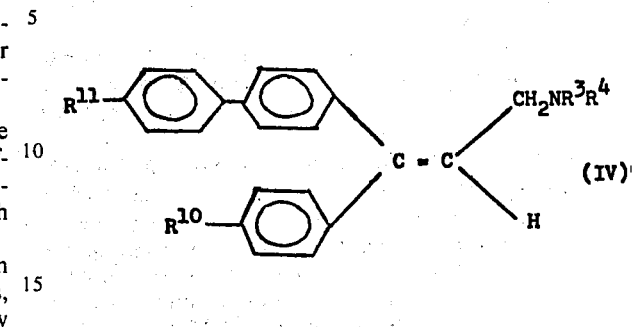
(IV)

where $R^3$ and $R^4$ are as defined above and $R^{10}$ and $R^{11}$ are the same or different and may each represent a hydrogen or halogen atom, or a cyano group or nitro group, have been found to be of notably high activity.

Compounds in which $R^1$ and $R^2$ are identical do not exhibit geometrical isomerism. In this class of compounds those in which $R^1$ and $R^2$ both represent biphenylyl, preferably 4-biphenylyl, groups are particularly of note. Three such compounds are 1, 1 — di (4 - biphenylyl)— 3- dimethylamino - prop - 1 -ene; 1, 1 - di(4 -biphenylyl) -3- methylamino - prop - 1- ene; and 1, 1 - di (4 - biphenylyl) - 3 - prop - 1 -ene.

In the above classes of compounds $R^3$ and $R^4$ may represent a hydrogen atom or an alkyl group having from 1 to 4 carbon atoms, with the proviso that both $R^3$ and $R^4$ should not represent hydrogen.

There is some evidence that as the size of the alkyl group in $R^3$ and/or $R^4$ is increased, the activity of the compounds tend to diminish. Accordingly, compounds where $R^3$ and $R^4$ represent hydrogen atoms and/or methyl groups are provided in a preferred embodiment of the invention. Compounds in which both $R^3$ and $R^4$ represent hydrogen atoms are particularly preferred.

In a further aspect of the present invention there is provided a method of preparing a compound of formula (I) as described above which comprises A. reacting a compound of formula (V)

(V)

where $R^1$ and $R^2$ are as defined above, as specified hereunder:

a. when Q and G taken together represent a single bond,
 i. when M represents a nitrile group; a group of formula $CYNR^3R^4$ where Y is an oxygen or sulphur atom; a group of formula $CH_2A$ where A represents the group —NC, —NR$^3$COR$^9$ or —NR$^3$COOR
    where R represents an alkyl group having from 1 to 4 carbon atoms and where $R^9$ represents a hydrogen atom or an alkyl group having from 1 to 3 carbon atoms; selectively reducing the compound so that the double bond in the $R^1R^2C = C$ moiety remains unreduced;

ii. when M represents a group of formula CH₂Z, where Z represents a readily displaceable group such as a bromo or tosyloxy group, reacting the compound of formula (V) with an amine of formula HNR³R⁴;

iii. when M represents a group of formula CH₂NR³R⁴, where one or both of R³ and R⁴ represent hydrogen atoms, mono or dialkylating the NR³R⁴ group; or iv. when M represents a group of formula CH₂NR³B where B is a protecting group, such as an acyl group, removing the protecting group;

b. or when Q represents a nucleophilic group, for example a hydroxy, chloro, bromo, iodo, acryloxy, sulphonyloxy, amino or substituted amino group, G represents a hydrogen atom and M represents a group of formula CH₂NR³R⁴ eliminating a molecule of GQ from a molecule of formula (V);

B. reacting a phosphorane of formula (VI)

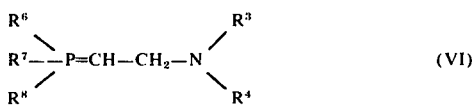

wherein R⁶, R⁷ and R⁸ are alkyl or phenyl groups, with a ketone of formula (VII)

C. or a combination of method A (a) (iii) with any other method. In the case where M represents a nitrile group and Q and G represent a single bond, the compound of formula (V) has the structure (IX) (c.f. method (A) (a) (i))

Reduction of this compound leads only to the primary amine of formula (I) where R³ and R⁴ both represent hydrogen atoms. This reduction can be carried out using the process described by Jones and Maisey in J. Med. Chem 1971, 14, 161.

When M represents the group CYNR³R⁴ and Q and G represent a single bond the compound of formula (V) has the structure

When Y is an oxygen atom, (X) then being an amide, reduction may be carried out, for example, by means of a metallic hydride, such as sodium borohydride, lithium aluminium hydride, or by diborane. When Y is a sulphur atom, reduction may be carried out, for example, by means of a Raney nickel catalyst. The amides can be prepared using a procedure similar to that outlined in Chemical Abstracts 65, 615 g. 1966. The corresponding sulphur compounds can be prepared by reacting the appropriate nitrile with hydrogen sulphide in ethanol under pressure or by reacting the corresponding amide with P₂S₅.

When M represents the group CH₂A and Q and G represent a single bond the compound of formula (V) has the structure (XII) (c.f. method (A) (a) (i))

The compounds can be obtained from the corresponding amines using any appropriate conventional technique known to those skilled in the art. Reduction can be accomplished using, for example, lithium aluminium hydride.

When M represents a group of formula CH₂Z and Q and G represent a single bond the compound of formula (V) has the structure (XIII) (c.f. method (A) (a) (i))

Compounds where Z represents a bromine atom can be prepared from the corresponding prop-1-ene using N - bromo succinimide and azobisisobutyronitrile. Compounds where Z represents a tosyloxy group can be prepared from the corresponding alcohol using p-toluene sulphonyl chloride. This alcohol, which has the structure R¹R²C = CH.CH₂OH can be prepared by the reduction of the α,β- saturated ester of formula R¹R²C = CHCO₂CH₃ which can itself be prepared by a Wittig reaction between a ketone of formula R¹R²CO and diethylphosphonoacetate.

When M represents a group of formula CH₂NR³R⁴ where one or both R³ and R⁴ represent hydrogen atoms, and Q and G represent a single bond, the compound of formula (V) has the structure (XI) (c.f. method (A) (a) (iii))

Mono or dialkylation of this compound, as appropriate, can be carried out by methods well-known in the art. For example, monoalkylation can be carried out using the Forster-Decker reaction (c.f. Name Index of Organic Reactions by Gowan and Wheeler, London 1960 Page 92). Complete alkylation can be carried out by treating the amine with a mixture of formaldehyde and formic acid. Obviously, this method can only be used to provide compounds of formula (I) in which one or both of R³ and R⁴ represent alkyl groups.

When M represents a group of formula CH₂NR³B and Q and G represent a single bond the compound of formula (V) can be represented by the formula (XIV) (c.f. method (A) (a) (iv))

As examples of protecting groups there may be mentioned acyl and phenyl groups (the former being removable by any technique conventional in the art and the latter being removable by nitrosation and subsequent treating with sodium hydroxide). These compounds of formula (XII) can be easily prepared from the corresponding amines using standard techniques.

When M represents a group of formula $CH_2NR^3R^4$, Q represents a nucleophilic group and G represents a hydrogen atom the compound of formula (V) can be represented by the formula (XV) (c.f. method (A) (b))

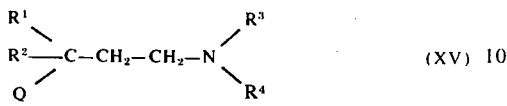 (XV)

In the above compound, it is preferred that Q be a hydroxyl group since the elements of water can be removed from such compounds simply by treatment with a strong acid as concentrated hydrochloric acid in glacial acetic acid. Thus, 1,1-di (4-biphenylyl) - 3 - dimethylamino-prop-1-ene can be prepared by the dehydration of 1,1-di(4-biphenylyl)-3 - dimethylamino-propan-1-ol. Compounds of formula (XV), where Q is a hydroxy group, can be prepared by the reaction of an organometallic reagent of formula $R^1Z$, where $R^1$ is as defined previously and where Z is, for example, a magnesium halide or lithium, with an ester of formula (XVI)

 (XVI)

or a ketone of formula (XVII)

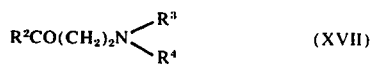 (XVII)

$R^5$ being an alkyl group, preferably one containing from 1 to 4 carbon atoms.

Compounds of formula (I) can also be prepared by a Wittig reaction between a phosphorane of formula

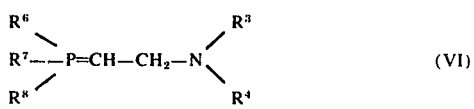 (VI)

and a ketone of formula

 (VII)

(c.f. method (B))
Standard Wittig reaction conditions known in the art can be used for this process. The phosphorane can be generated, in situ if desired, by the reaction of an appropriate phosphonium halide with a strong base, such as an organometallic compound, e.g. butyl lithium.

The ketones of formula (vII) where $R^1$ and $R^2$ do not both represent biphenylyl groups are novel compounds. For example the class of intermediate ketones of formula (XVIII).

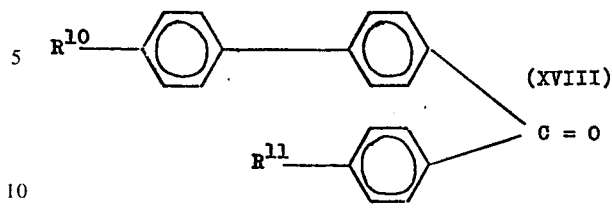

where $R^{10}$ and $R^{11}$ are as defined above are novel.

These novel ketones may be prepared by any suitable method, for example by a Friedel-Crafts reaction between an appropriately substituted biphenyl derivative and a benzoyl chloride or by a Friedel-Crafts reaction between an acid chloride of formula (XIX)

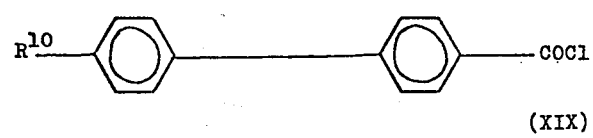

and an appropriately substituted benzene derivative.
Alternatively, they may be prepared by the halogenation, for example chlorination or bromination, or nitration of the 4-biphenylyl phenyl ketone or an appropriate monosubstituted derivative thereof.

In the above process, products where $R^1$ and $R^2$ are different exhibit geometrical isomerism. The cis and trans isomers can be separated using, for example, fractional crystallisation of the bases, hydrochlorides or oxalates. Alternatively, in some cases a base exchange resin may be used to effect the desired separation.

When the preparation of compounds of formula (I), where both $R^3$ and $R^4$ represent hydrogen atoms is envisaged, the preferred routes of preparation are those classified under the headings (A) (a) (i), (A) (a) (ii) or (A) (a) (iv), as defined above.

The intermediates of formula (VI), where one of $R^3$ represents an alkyl group having from 1 to 4 carbon atoms and $R^4$ represents a hydrogen atom; of formula VIII and formula (V); and of formula (VII), where both of $R^1$ and $R^2$ do not represent unsubstituted biphenylyl groups are novel compounds and are therefore provided in a further aspect of the invention.

The present invention also provides a pharmaceutical formulation which comprises a substituted 3 - amino - prop -1 - ene of formula (I), or a pharmaceutically acceptable salt thereof, together with a pharmaceutically acceptable carrier therefor.

The preferred pharmaceutically acceptable salt is the hydrochloride.

In a further aspect of the invention there is provided a method of preparing a pharmaceutical formulation as defined above which comprises bringing into association the substituted 3-amino-prop-1 1-ene of formula (I), or pharmaceutically acceptable salt thereof, and the pharmaceutically acceptable carrier therefor.

As stated above, the compounds of formula (I) may be presented in a pharmaceutical composition for administration to a host infected with *T. cruzi*. They may be made by admixture of the components using any conventional technique used for making such compositions.

A compound of formula (I) may thus be presented in discrete units, such as tablets, capsules, cachets or ampoules each containing a predetermined quantity of the compound. These compositions may include one or more of the following carriers; solid diluents, flavouring, binding, dispersing, surface active, thickening, and coating materials and preservatives, antioxidants and bacteriostats.

A preferred mode of presentation is a tablet which may be produced by granulating the active ingredient with a diluent and, preferably, a lubricant and compressing the granules into tablets. Compositions for subcutaneous administration are also another preferred mode of presentation and these may be made by presenting the compound as a sterile powder in a sealed container for dilution with sterile water.

For use in treating human infections of T. cruzi, it is estimated from data obtained from in vivo experiments with mice that doses which could be administered daily are of the order of 5 mg to 500 mg/kg, preferably 25 mg to 200 mg/kg, more preferably 50 mg to 100 mg/kg. For example, it is estimated that a dose of 50 mg/kg given daily for a month will prove effective against infections of *T. cruzi*.

Naturally, the dosage levels indicated above will be varied at the discretion of the physician according to the degree of infection and other attendant circumstances.

The invention will now be illustrated with reference to the following Examples.

EXAMPLE 1

To β-dimethylaminoethyltriphenylphosphonium bromide (45.6 g.) stirred under nitrogen in dry ether (200 ml.) was added at room temperature a solution of butyl lithium (1.42 N; 77.0 ml.) in petroleum ether (b.p. 60°–80°C). After stirring for ten minutes, a suspension of di-4-biphenylyl ketone (33.4 g.) in dry benzene (400 ml.) was added over 10 minutes. The mixture was brought to the boil and solvent (320 ml.) distilled off while dry benzene (200 ml.) was simultaneously added. The mixture was boiled under reflux for 5 hours, cooled and decomposed by cautious addition of water (100 ml.) and 2NHCl (100 ml.). After standing at 0°C overnight the crude 1, 1-di(4-biphenylyl)-3-dimethylamino-prop-1-ene hydrobromide was filtered off, washed with benzene, ether and water, and converted to the base, which solidified. After recrystallisation from light petroleum (b.p. 40°–60°C) it had m.p. 94°–95°C. The hydrochloride crystallised from ethanol as colourless prisms, m.p. 228°C. The hydrochloride monohydrate crystallised from aqueous ethanol as needles m.p. indefinite.

The required β-dimethylaminoethyltriphenylphosphonium bromide was prepared by the method described in British Patent Specification No. 1,161,201, and di-4-biphenylylketone by the method of Matveev et al., Chemical Abstracts 55, 6434[b].

EXAMPLE 2

From β-diethylaminoethyltriphenylphosphonium bromide (prepared by the method described in British Patent Specification NO. 1,161,201) there was prepared, by the method of Example 1, 1,1-di(4-biphenylyl)-3-diethylaminoprop-1-ene hydrochloride, prisms from ethanol, m.p. 183°C.

EXAMPLE 3

To the Grignard reagent prepared from magnesium (7.3 g.) and 4-bromodiphenyl (69.9 g.) in ether (300 ml.) was added, at 0°C, ethyl β-dimethylaminopropionate (14.5 g.) in ether (50 ml.). After stirring under reflux for 3 hours the mixture was cooled and decomposed by addition of water (50 ml.), 25% aqueous ammonium chloride (50 ml.) and glacial acetic acid (42 ml.)

After standing overnight at 0°C, the crude 1, 1-di(4-biphenylyl)-3-dimethylamino-propan-1-ol hydrobromide was filtered off and washed with ether and water. The base, recrystallised from ethanol, had m.p. 160°C.

The carbinol base (15 g.) was boiled under reflux for half an hour with glacial acetic acid (100 ml.) and concentrated hydrochloric acid (30 ml.). The solvent was removed in vacuo and the residue basified to give 1, 1-di (4-biphenylyl)-3-dimethylaminoprop-1-ene, m.p. 94°–95°C, after recrystallisation from light petroleum (b.p. 40°–60°C). The hydrochloride (colourless prisms from ethanol, m.p. 228°C.) was identical with that described in Example 1.

EXAMPLE 4

From ethyl β-methylaminopropionate by the method of Example 3 was prepared 1,1-di(4-biphenylyl)-3-methylaminopropan-1-ol, needles from benzene, m.p. 154°–156°C. On dehydration this gave 1, 1-di(4-biphenylyl)-3-methylaminoprop-1-ene m.p. 94°C. Its hydrochloride monohydrate, needles from ethanol, had m.p. 160°C.

EXAMPLE 5

β-Methylaminoethyltriphenylphosphonium bromide was reacted with di-4-biphenylyl ketone by the method of Example 1 to give 1,1-di(4-biphenylyl-3-methylaminoprop-1-ene identical with that described in Example 4.

The required β-methylaminoethyltriphenylphosphonium phosphonium bromide was prepared by heating a mixture of β-phenoxyethyltriphenyl phosphonium-bromide (46.2 g.) dissolved in ethanol (80 ml.) and 33% ethanolic methylamine (130 ml.) in an autoclave at 100°C for three hours. After cooling, the product was precipitated by addition of dry ether (2 l.) filtered, washed with ether and dried, and had a melting point of 226°C.

EXAMPLE 6 p-Chlorobenzoyl chloride (43.8 g.) was added dropwise to a stirred mixture of fluorene (41.5 g.) aluminium chloride (33.4 g.) and carbon disulphide (100 ml.). After the vigorous reaction had subsided the mixture was stirred and boiled under reflux for 6 hours. It was cooled, poured onto ice, the carbon disulphide distilled off on a steam bath, and the solid product filtered off, washed, dried and recrystallised from benzene to give 2-p-chlorobenzoylfluorene, m.p. 183°C. This was reacted by the method of Example 1 to give trans-1-(2-fluorenyl)-1-p-chlorophenyl3-dimethylaminoprop-1-ene, hydrochloride from ethanol, m.p. 236°–237°C. Isomeric homogeneity was confirmed by n.m.r. spectroscopy.

EXAMPLE 7 p-Iodobenzoyl chloride was reacted with 4-chlorobiphenyl by the method of Example 6 to give 4'-chloro-4-biphenylyl p-iodophenyl ketone, m.p. 218°C after recrystallisation from benzene.

EXAMPLES 8 to 18

Using the procedure described in Example 7 the following ketones were prepared, each having the formula where $R^1$ and $R^2$ are as identified in the following Table:

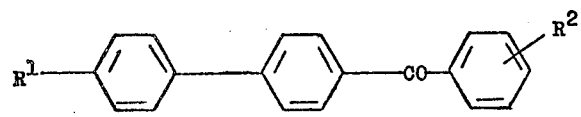

| Example No. | $R^1$ | $R^2$ | Melting point of ketone, °C |
|---|---|---|---|
| 8 | Cl | p-Cl | 187 |
| 9 | Cl | p-Br | 197 |
| 10 | Br | p-Cl | 194 |
| 11 | Br | p-Br | 212 |
| 12 | Cl | p-F | 166 |
| 13 | Cl | p-NO$_2$ | 128 |
| 14 | I | p-Cl | 213 |
| 15 | I | p-I | 265 |
| 16 | Cl | o-Br | 145 |
| 17 | Br | o-Cl | 158 |
| 18 | Cl | m-Br | 144 |

EXAMPLE 19

4'-Chloro-4-biphenylyl p-chlorophenyl ketone, prepared by the process of Example 8, (19.6 g.) was treated with the phosphorane derived from β-dimethylaminoethyltriphenylphosphonium bromide (27.3 g.) by the method described in Example 1. After decomposition and standing overnight at 0°C, the mass of colourless needles of the mixed hydrobromides of the two geometrical isomers of 1-(4'-chloro-4-biphenyl)-1-p-chlorophenyl-3-dimethylaminoprop-1-ene was filtered off, washed with benzene, water and ether and converted to mixed isomer bases. This partially solidified and after several recrystallisations (ethanol) gave trans 1-(4'-chloro-4-biphenylyl)-1-p-chlorophenyl-3-dimethylaminoprop-1-ene (the dimethylamino group is trans to the biphenylyl group) as colourless prisms, m.p. 139°C, hydrochloride from ethanol, m.p. 245°C. The ethanol filtrate from the first recrystallisation was taken to dryness and the mixture of cis-1-(4'-chloro-4-biphenylyl)-1-p-chlorophenyl-3-dimethylaminoprop-1-ene and triphenylphosphine oxide was converted to hydrochloride in ether. Recrystallisation from ethanol gave cis-1-(4'-chloro-4-biphenylyl)-1-p-chlorophenyl-3 -dimethylaminoprop-1-ene hydrochloride triphenylphosphine oxide complex, prisms, m.p. 191°C. It was reconverted to base and thence to the acid oxalate m.p. 215°–216°C, which separated from ethanol free of triphenylphosphine oxide. Appropriate manipulation gave cis-1-(4'-chloro-4-phenylyl)-1-p-chlorophenyl-3-dimethylaminoprop-1-ene hydrochloride, matted needles from ethanol/ether, m.p. 205°C. N.m.r. spectroscopy showed both the trans and cis isomers to be isomerically homogeneous.

EXAMPLE 20

The ketone prepared in Example 7 was reacted with the phosphorane of Example 19 using the procedure described in Example 19, with minor modifications to take into account the relative solubilities of the bases, hydrochlorides, hydrochloride — triphenylphosphine oxide complexes and acid oxidates of the isomers of the final product.

Thus were obtained trans-1-(4'-chloro-4-biphenylyl)-1-p-iodophenyl -3-dimethylaminoprop-1-ene hydrochloride (m.p. 235°C) and cis-1-(4'-chloro-4-biphenylyl)-1-p-iodophenyl3-dimethylaminoprop-1-ene oxalate (m.p. 188°C). The hydrochloride from ethanol/ether has m.p. 225°C. and N.m.r. spectroscopy showed it to have an isomeric purity of <96%.

EXAMPLES 21 to 23

The procedure of Example 19 was repeated, with slight modifications as indicated in Example 20, using various of the ketones of Examples 9 to 15. The structures and melting points of the prop-1-enes obtained were as indicated in the following Table.

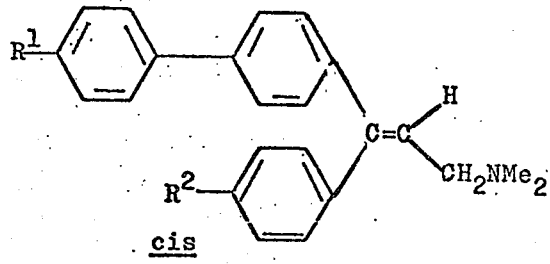

trans

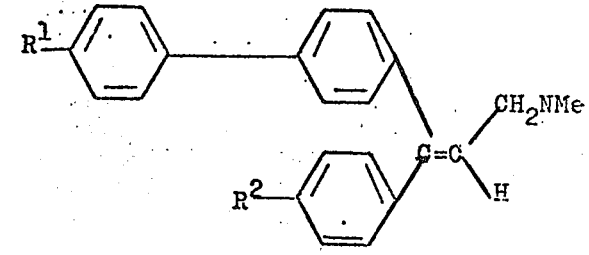

cis

| Ex. No. | $R^1$ | $R^2$ | BASE/salt | trans m.p.°C | isomeric purity%* | base/salt | cis m.p. °C | isomeric purity%* |
|---|---|---|---|---|---|---|---|---|
| 21 | Cl | Br | base | 90 | 83 | oxalate | 205 | 88 |
| 22 | Br | Br | base | 137 | >98 | oxalate | 197 | 63 |
| 23 | I | I | base | 200 | >98 | base | 114 | 85 |

*by n.m.r. spectroscopy

The configuration of the isomers described in Examples 19 – 23 is assigned from their ultra violet spectra. The tans isomers, in which the biphenylyl group is free to assume the plane of the double bond, exhibit a u.v. spectrum closely resembling that of 4-vinylbiphenyl. The cis isomers, in which the biphenylyl group is hindered, show a maximum u.v. absoprtion at lower wavelength, in which contributions from the p-halogenostyrene and biphenyl chromophores can be discerned.

EXAMPLES 24 –29

The procedure of Example 19 was repeated with the appropriate ketone, with slight modification as appropriate, to give the 3-dimethylaminoprop-1-ene isomers listed in the following Table:

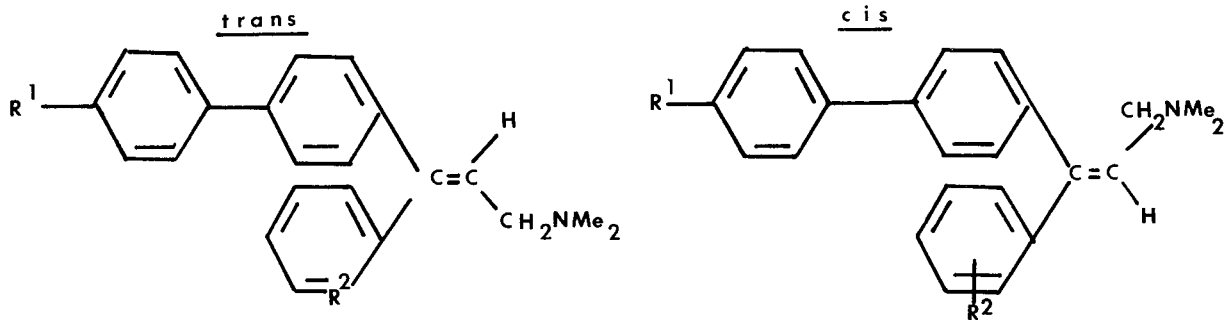

| Ex. No. | R¹ | R² | trans base/salt | trans m.p.°C | isomeric purity %* | cis base/salt | m.p.°C | isomeric purity %* |
|---|---|---|---|---|---|---|---|---|
| 24 | H | H | HCl | 225 | >98 | HCl | 170 | 88 |
| 25 | H | p-Cl | HCl | 241 | >98 | oxalate | 187 | 78 |
| 26 | H | p-Br | HCl | 235 | >98 | HCl | 200 | 86 |
| 27 | H | p-I | HCl | 232 | >98 | base HCl | 114 224 | >98 |
| 28 | H | o-Br | oxalate | 145 | 78 | oxalate | 183 | >98 |
| 29 | H | o-Ph | oxalate | (mixed isomers 63:37)m.p.158–170°C | | | | |

*by n.m.r. spectroscopy

The ketones used in Examples 24 – 29 were prepared as follows: phenyl 4-biphenylyl ketone by the method of Montagne, Rec. Trav. Chim., 27, 357; p-chlorophenyl 4-biphenylyl ketone, Schoepfle and Trapp, J.A.C.S.., 54, 4064; 8-bromophenyl 4-biphenylyl ketone and p-bromophenyl 4-biphenylyl ketone, Gomberg and Bailar, J.A.C.S. 51, 2233; p-Iodophenyl 4-biphenylyl ketone, m.p. 211°C prepared by the method of Example 7. 4-Biphenylyl 2-biphenylylketone, m.p. 110°C, yellow prisms from ethanol, was prepared by Grignard reaction of 4-biphenylyl magnesium bromide with 2-cyanobiphenyl, following the method of Tchitchibabin and Koragin, Chem. Zent., 1914, 1658.

EXAMPLE 30

4'-Chlorobiphenyl-4-carboxylic acid chloride (Musante and Parrini, Gazz, Chim. ital., 1949, 49, 453) was reacted with chlorobenzene by the method of Example 7, to give 4-chlorophenyl 4'-chloro-4-biphenylyl ketone identical with that described in Example 8.

EXAMPLE 31

Di-4-biphenylyl ketone (6.68 g.) was added to a mixture of N,N-Di-methylcarbamoylmethyl phosphonic acid diethyl ester (C.A. 65, 615 g. 1966) (4.46 g.), sodium hydride (60%) (0.8 g.) and benzene (400 ml.). The mixture was boiled under reflux for sixty hours. The benzene layer, decanted and evaporated, gave an oil, from which, by column chromatography on silica gel MFC in benzene and elution by ethyl acetate, was isolated N,N-dimethyl3, 3-di(4-biphenylyl) acrylamide, m.p. 121°C after recrystallisation from light petroleum (b.p. 80°–100°C). This, reduced with lithium aluminium hydride in ether/tetrahydrofuran at –30°C, gave 1,1-di(4-biphenylyl) -3 -dimethylaminoprop-1-ene identical with that described in Example 1 .

EXAMPLE 32

Di-4-biphenylyl ketone was reacted with acetonitrile in benzene in the presence of sodamide by the method of Lettre and Wick (Annalen, 1957, 603, 194) to give 3-hydroxy3, 3-di(4-biphenylyl) propionitrile, m.p. 168°–170°C, after recrystallisation from benzene. The nitrile (8.0 g.) dissolved in a mixture of tetrahydrofuran (80 ml.) and ether (80 ml.) was added over 30 minutes at room temperature under nitrogen to a stirred suspension of lithium aluminium hydride (2.88 g.) in ether (75 ml.). After stirring a further hour the mixture was decomposed by addition of water (2.8 ml.) and aqueous N sodium hydroxide (12 ml.) After filtration, the organic layer was separated and evaporated to give a solid which recrystallised from benzene/light petroleum (b.p. 80°–100°C), gave 1,1-di(4-biphenylyl)-3-aminopropan-1-ol, prisms, m.p. 176°–8°C, λmax (ethanol) = 260 nm. The carbinol (6.5 g.) boiled under reflux for one hour with glacial acetic acid (40 ml.) and concentrated hydrochloric acid (10 ml.) gave 1, 1-di-(4-biphenylyl)-3-aminoprop-1-ene hydrochloride, needles from n-propanol, m.p. 231°–232°C. The base, from ethanol, had m.p. 127°–8°C,λmax (ethanol) = 274 nm.

EXAMPLE 33

1, 1-Di(4-biphenylyl)-3-aminoprop-1-ene base (Example 32) (3.61 g.) and 35% aqueous formaldehyde (1. 9 g.) were added to formic acid (2.6 g.). The mixture was boiled under reflux for 12 hours. Concentrated hydrochloric acid ( 1 ml.) was added, the mixture evaporated to dryness and the solid residue recrystallised from ethanol to give 1,1-Di(4-biphenylyl)-3-dimethylaminoprop-1-ene hydrochloride, identical with that described in Example 1.

EXAMPLE 34

1, 1-Di(4-biphenylyl)-3-aminoprop-1-ene base (Example 32) (3.61 g.) and benzaldehyde (1.06 g.) were dissolved in ethanol (25 ml.) and boiled under reflux for 1 hour. After removal of solvent, methyl iodide (1.5 g.) was added and the mixture heated in a stoppered flask for 5 hours at 100°C. The viscous product was boiled under reflux with 90% aqueous ethanol (25 ml.) for one hour, ethanol and benzaldehyde were removed by steam distillation, the residue made alkaline with ammonia, and the liberated base isolated with ether. Converted to hydrochloride and recrystallised from ethanol, it gave, 1, 1-di(4-biphenylyl)-3-methylaminoprop-1-ene hydrochloride identical with that described in Example 3.

EXAMPLE 35

To 1, 1-di(4-biphenylyl)prop-1-ene (Pfeiffer and Schneider, J. prakt. chem., 1931, 129, 129) (0.85 g.) in carbon tetrachloride (25 ml.) heated under nitrogen at 50°C were added finely ground N-bromo succinimide (0.45 g.) and azobisisobutyronitrile (50 mg.) and the mixture stirred at 50°C for 24 hours. The succinimide formed was filtered off, and the filtrate evaporated to give 1, 1-di(4-biphenylyl)-3-bromoprop-1-ene as a cream solid. It was dissolved in acetone (10 ml.) and 25% aqueous dimethylamine (1 ml.) The mixture was warmed on the steam bath for 10 minutes and the solvent evaporated. The residue was dissolved in ether, the ether solution washed twice with water, dried and acidified with ethereal HCl. The precipitated hydrochloride was filtered off and recrystallised from ethanol to give 1,1-di(4-biphenylyl)-3-dimethylaminoprop-1-ene hydrochloride identical with that described in Example 1.

Examples 36 – 39

The procedure of Example 19, with slight modifications as indicated in Example 20 was employed to prepare, inter alia, cis - isomers of formula:

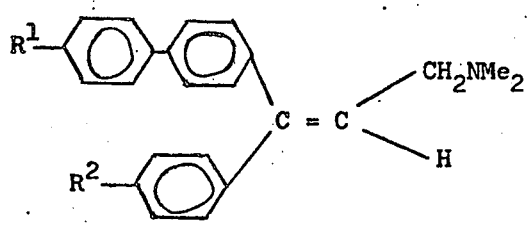

having the structures and physical properties set out in the following Table.

| Ex. No. | R¹ | R² | base/salt | m.p.°C | isomeric purity %* |
|---|---|---|---|---|---|
| 36 | Br | Cl | Oxalate | 214 | >98 |
| 37 | Cl | F | Oxalate | 213 | >98 |
| 38 | Cl | NO₂ | Base | 110 | 73 |
| 39 | I | Cl | Oxalate | 177 | 82 |

*by n.m.r. spectroscopy

The ketones used in Examples 36 to 39 were those of Examples 10, 12, 13 and 14 respectively.

EXAMPLES 40 and 41

The procedure of Example 19 was repeated with slight modifications as indicated in Example 20, using each of the ketones of Examples 16 and 18. The structures and melting points of the prop -1 - enes -enes obtained were:

| Ex. No. | R¹ | R² | |
|---|---|---|---|
| 40 | Cl | o-Br | Trans-isomer oxalate m.p. 150°C 91% pure. cis-isomer oxalate, m.p. 214°C 98% pure. |
| 41 | Cl | m-Br | Mixed isomer oxalates (50:50),m.p. 163-186°C |

EXAMPLE 42

To sodium hydride (60%) (3.75 g.), suspended in dry dimethoxyethane (75 ml.) and stirred under N₂ was added dropwise at 0°C diethoxyphosphono-acetonitrile (15.9.g.) followed by a suspension of dibiphenylyl ketone (25 g.) in dimethoxyethane (200 ml.) over one hour. Stirring was continued for one hour at room temperature and a further hour at 50°–60°C. The mixture was cooled, decomposed by addition of water, extracted with ether, the solvent removed, and the residual solid recrystallised from n-propanol/benzene to give 3,3-di(4biphenylyl) acrylonitrile, m.p. 154°C. This was reduced with lithium aluminium hydride at —20°C by the method of Jones, Maisey et al., (J.Med.-Chem., 1971, 14, 161) to give material from which 1, 1-di(4-biphenylyl) -3-aminoprop1-ene identical with that described in Example 32 could be isolated by preparative layer chromatography.

EXAMPLE 43

Acetic anhydride (1ml) was added to a solution of 1, 1 - di(4 - biphenylyl 3 - amino - prop - 1 -ene (1g) in 99% formic acid (5ml) and the mixture was refluxed for 1 hour then poured onto ice. The solid was collected, washed with water, dried and then recrystallised from benzene/ n - propanol to furnish 1, 1-di(4 biphenylyl) -3 - formamido - prop - 1 ene (m.p. 171°–173°C). This compound, reduced with lithium aluminium hydride in ether/tetrahydrofuran at −30°C, afforded 1, 1-di (4 -biphenylyl -3 - methylamino - prop- 1 - ene identical with that described in Example 4.

EXAMPLE 44

1, 1 - di (4 - biphenylyl) -3 - amino - prop -1 -ene (1g) was added to a mixture of anhydrous sodium acetate (1g), acetic acid (10 ml) and acetic anhydride (1 ml) and the mixture was refluxed for one hour then evaporated in vacuo. The residue was washed with water and dried and recrystallised from n - propanol to give 1, 1-di (4-biphenylyl) -3 - acetamido - prop -1 - ene. (m.p. 246°– 249°C). This compound was reduced in a similar manner to the method described in Example 43 to yield 1, 1 - di (4-biphenylyl) -3 - ethylamino - prop -1 - ene.

EXAMPLE 45

A tablet containing 1, 1 - di (4 - biphenylyl) -3 dimethylamino - prop -1 - ene was made up from the following components.

| (I) 1,1-di(4-biphenylyl)-3-dimethylamino-prop-1-ene | 250 mg. |
|---|---|
| (II) Lactose B. P. | 125 mg. |
| (III) Starch B. P. | 40 mg. |
| (IV) Methyl hydroxyethyl cellulose | 6 mg. |
| (V) Magnesium stearate B. P. | 2 mg. |

Components (I) and (II) were granulated and mixed together with a 5% solution of component (IV) in 50% aqueous alcohol. The granules were dried at 50°C and components (III) and (V) added. Mixing was then carried out, followed by compression into tablets.

EXAMPLE 46

A hard capsule containing 1, 1 - di (4-biphenylyl) -3 - dimethylamino - prop -1 - ene was formed from the following components.

| (I) 1,1-di(4-biphenylyl)-3-dimethylamino-prop-1-ene | 100 mg. |
|---|---|
| (II) Talc B. P. | 10 mg. |
| (III) Starch B. P. | 40 mg. |

Component (I) was ground up and then mixed with components (II) and (III). The mixed powder was used to fill hard gelatin capsules.

EXAMPLE 47

A tablet containing cis-1-(4'-chloro-4-biphenylyl) -1 - p - chlorophenyl -3 - dimethylamino prop -1 - ene hydrochloride as the active ingredient was made up from the following ingredients.

| (I) Cis-1-(4'-chloro-4-biphenylyl) -1-p-chlorophenyl-3- dimethylamino-prop-1-ene hydrochloride | 500 mg. |
| (II) Microcrystaleine cellulose | 150 mg. |
| (III) Starch B. P. | 50 mg. |
| (IV) Gelatin B. P. | 10 mg. |
| (V) Magnesium stearate B. P. | 2 mg |

Component (I) was granulated with half of components (II) and (III) with a 10% solution of component (IV) in 50% aqueous alcohol. The mixture was dried at 50°C. The remainder of components (II) and (III) and also component (V) were then added to the dried granules and mixing carried out. The mixture was then compressed into tablets.

EXAMPLE 48

A syrup was made up from the following ingredients.

| (I) Cis-1-(4'-chloro-4-biphenylyl) -1-p-chlorophenyl-3-dimethylamino- prop-1-ene hydrochloride | 500 mg. |
| (II) Sucrose B. P. | 30 g. |
| (III) Glycerin B. P. | 15 g. |
| (IV) Methyl hydroxybenzoate B. P. | 0.1 g. |
| (V) Saccharin Sodium B. P. | 0.1 g. |
| (VI) Amaranth B. P. C. 1954 | 1.0 mg. |
| (VII) Purified water B. P. | to 100 ml. |

Components (II) (IV) and (V) were dissolved in purified water and components (III) and (VI) then added. To this aqueous mixture was added component (I) which was dissolved therein. Sufficient purified water was then added to adjust the volume to 100 ml. After filtration, the syrup was ready for use.

What is claimed is:

1. A pharmaceutical composition for use in treating infections caused by Trypanosoma cruzi comprising a compound of formula (I)

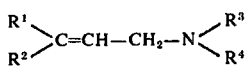

wherein $R^1$ and $R^2$ are the same or different and can each represent a substituted or unsubstituted biphenylyl or fluorenyl group, or one only of $R^1$ and $R^2$ can represent a substituted or unsubstituted phenyl group, with the proviso that both $R^1$ and $R^2$ cannot represent a substituted biphenylyl gruop and that when one of $R^1$ and $R^2$ represents a substituted biphenylyl group, the other represents a substituted or unsubstituted phenyl group, provided that when $R^1$ or $R^2$ are substituted biphenylyl, phenyl or fluorenyl they are substituted with halogen or nitro and wherein $R^3$ and $R^4$ are the same or different and are selected from the group consisting of a hydrogen atom, an alkyl group having from 1 to 4 carbon atoms and a benzyl group; or a pharmaceutically acceptable salt thereof in an amount effective to treat infections of Trypanosoma cruzi, in association with a pharmaceutically acceptable carrier therefor.

2. The composition as defined in claim 1 wherein $R^1$ represents a substituted or unsubstituted biphenylyl group and $R^2$ represents a substituted or unsubstituted phenyl group.

3. The composition as defined in claim 2 wherein $R^1$ represents a substituted or unsubstituted 4-biphenylyl group.

4. The composition as defined in claim 3 wherein $R^3$ and $R^4$ both represent hydrogen atoms.

5. The composition as defined in claim 4 wherein the substitution in the phenyl or biphenylyl groups in in the para position.

6. The composition as defined in claim 3 wherein $R^3$ and $R^4$ are selected from the group consisting of a hydrogen atom, and an alkyl group having from 1 to 4 carbon atoms, with the proviso that both of $R^3$ and $R^4$ cannot represent hydrogen atoms.

7. The composition as defined in claim 2 wherein the biphenylyl and $CH_2NR^3R^4$ groups are in a cis relationship.

8. The composition as defined in claim 6 wherein $R^3$ and $R^4$ both represent methyl groups.

9. The composition as defined in claim 1 in which the compound of formula I is cis-1-(4'-chloro-4-biphenylyl)-1-p-iodophenyl-3-dimethylaminoprop-1-ene; cis-1-(4'-chloro-4-biphenylyl)-1-p-bromophenyl-3-dimethylaminoprop-1-ene; cis-1-(4'-bromo-4-biphenylyl)-1-p-chlorophenyl-3-dimethylaminoprop-1-ene; cis-1-(4'-bromo-4-biphenylyl)-p-bromophenyl-3-dimethylaminoprop-1-ene; cis-1-(4'-chloro-4-biphenylyl)-1-p-chlorophenyl-3-dimethylaminoprop-1-ene; cis-1-(4'-chloro-4-biphenylyl)-1-p-fluorophenyl-3-dimethylaminoprop-1-ene; or cis-1-(4'-chloro-4-biphenylyl)-p-nitrophenyl-3-dimethylaminoprop-1-ene.

10. The composition as defined in claim 1 wherein both of $R^1$ and $R^2$ represent unsubstituted biphenylyl groups.

11. The composition as defined in claim 10 wherein the biphenylyl groups are 4-biphenylyl groups.

12. The composition as defined in claim 11 wherein $R^3$ and $R^4$ are selected from the group consisting of a hydrogen atom and an alkyl group having from 1 to 4 carbon atoms, with the proviso that both of $R^3$ and $R^4$ cannot represent hydrogen atoms.

13. The composition as defined in claim 10 wherein $R^3$ and $R^4$ both represent hydrogen atoms.

14. The composition as defined in claim 10 wherein $R^3$ and $R^4$ both represent methyl groups.

15. The composition as defined in claim 1 in which the compound of formula 1 is 1,1-di(4-biphenylyl)-3-dimethylamino-prop-1-ene.

16. The composition as defined in claim 1 in which the compound of formula 1 is 1,1-di(4-biphenylyl)-3-aminoprop-1-ene.

17. A method of treating a human infected with *Trypanosoma cruzi* which comprises administering to the infected human an effective *Trypanosoma cruzi* infection treatment amount of a compound of formula I

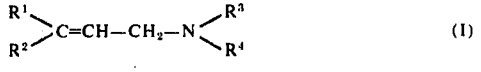

wherein $R^1$ and $R^2$ are the same or different and can each represent a substituted or unsubstituted biphenylyl or fluorenyl group, or one only of $R^1$ and $R^2$ can represent a substituted or unsubstituted phenyl group, with the proviso that both $R^1$ and $R^2$ cannot represent a substituted biphenylyl group and that when one of $R^1$ and $R^2$ represents a substituted biphenylyl group, the other represents a substituted or unsubstituted phenyl group, provided that when $R^1$ or $R^2$ are substituted biphenylyl, phenyl or fluorenyl they are substituted with halogen or nitro and wherein $R^3$ and $R^4$ are the same or different and are selected from the group consisting of a hydrogen atom, an alkyl group having from 1 to 4 carbon atoms and a benzyl group; or a pharmaceutically acceptable salt thereof.

18. The method as defined in claim 17 wherein $R^1$ represents a substituted or unsubstituted biphenylyl group and $R^2$ represents a substituted or unsubstituted phenyl group.

19. The method as defined in claim 18 wherein $R^1$ represents a substituted or unsubstituted 4-biphenylyl group.

20. The method as defined in claim 19 wherein $R^3$ and $R^4$ both represent hydrogen atoms.

21. The method as defined in claim 20 wherein the substitution in the phenyl or biphenyl groups is in the para position.

22. The method as defined in claim 19 wherein $R^3$ and $R^4$ can each represent either a hydrogen atom, or an alkyl group having from 1 to 4 carbon atoms, with the proviso that both of $R^3$ and $R^4$ cannot represent hydrogen atoms.

23. The method as defined in claim 18 wherein the biphenylyl and $CH_2NR^3R^4$ groups are in a cis relationship.

24. The method as defined in claim 22 wherein $R^3$ and $R^4$ both represent methyl groups.

25. The method as defined in claim 17 in which the compound of formula I is cis-1-(4'-chloro-4-biphenylyl)-1-p-iodophenyl-3-dimethylaminoprop-1-ene; cis-1-(4'-chloro-4-biphenylyl)-1-p-bromophenyl-3-dimethylaminoprop-1-ene; cis-1-(4'-bromo-4-biphenylyl)-1-p-chlorophenyl-3-dimethylaminoprop-1-ene; cis-1-(4'-bromo-4-biphenylyl)-p-bromophenyl-3-dimethylaminoprop-1-ene; cis-1-(4'-chloro-4-biphenylyl)-1-p-chlorophenyl-3-dimethylaminoprop-1-ene; cis-1-(4'chloro-4-biphenylyl)-1-p-fluorophenyl-3-dimethylaminoprop-1-ene; or cis -1-(4'-chloro-4-biphenylyl)-p-nitrophenyl-3-dimethylaminoprop-1-ene.

26. The method as defined in claim 17 wherein both of $R^1$ and $R^2$ represent unsubstituted biphenylyl groups.

27. The method as defined in claim 26 wherein the biphenylyl groups are 4-biphenylyl groups.

28. The method as defined in claim 27 wherein $R^3$ and $R^4$ are selected from the group consisting of a hydrogen atom and an alkyl group having from 1 to 4 carbon atoms, with the proviso that both of $R^3$ and $R^4$ cannot represent hydrogen atoms.

29. The method as defined in claim 26 wherein $R^3$ and $R^4$ both represent hydrogen atoms.

30. The method as defined in claim 26 wherein $R^3$ and $R^4$ both represent methyl groups.

31. The method as defined in claim 17 in which the compound of formula I is 1,1-di(4-biphenylyl)-3-dimethylaminoprop-1-ene.

32. The method as defined in claim 17 in which the compound of formula I is 1,1-di(4-biphenylyl)-3-aminoprop-1-ene.

33. The method of claim 17 in which the amount is 5 to 500 mg/kg.

34. The method of claim 33 in which the amount is 25 to 200 mg/kg.

35. The method of claim 34 in which the amount is 50 to 100 mg/kg.

36. The method of claim 17 in which the compound or the salt thereof is administered orally or subcutaneously.

* * * * *